(12) United States Patent
Weitzig et al.

(10) Patent No.: US 8,504,173 B2
(45) Date of Patent: Aug. 6, 2013

(54) ELECTRODE CATHETER, IN PARTICULAR FOR CARDIAC THERAPY

(75) Inventors: Pierre Weitzig, Berlin (DE); Jochen Palm, Mahlow (DE); Detmar Jadwizak, Erkner (DE); Carsten Fruendt, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 73 days.

(21) Appl. No.: 13/205,232

(22) Filed: Aug. 8, 2011

(65) Prior Publication Data
US 2012/0053668 A1 Mar. 1, 2012

Related U.S. Application Data

(60) Provisional application No. 61/378,406, filed on Aug. 31, 2010.

(51) Int. Cl.
*A61N 1/00* (2006.01)

(52) U.S. Cl.
USPC .......................................... 607/122

(58) Field of Classification Search
USPC .......................................... 607/122
See application file for complete search history.

(56) References Cited

U.S. PATENT DOCUMENTS

| | | | |
|---|---|---|---|
| 4,592,372 A | 6/1986 | Beranek | |
| 5,330,522 A | 7/1994 | Kreyenhagen | |
| 5,417,208 A * | 5/1995 | Winkler | 600/374 |
| 2002/0055764 A1 | 5/2002 | Malonek et al. | |
| 2003/0009094 A1* | 1/2003 | Segner et al. | 600/374 |
| 2004/0064174 A1 | 4/2004 | Belden | |
| 2005/0004642 A1 | 1/2005 | Shoberg | |
| 2006/0037195 A1 | 2/2006 | Bauer et al. | |

OTHER PUBLICATIONS

European Search Report and Notes to the European Search Report on European Patent Application No. EP 11 17 6444, dated Oct. 4, 2011 (7 pages).

* cited by examiner

*Primary Examiner* — George Manuel
(74) *Attorney, Agent, or Firm* — Buchanan Ingersoll & Rooney PC

(57) ABSTRACT

An electrode catheter, in particular for cardiac therapy, includes an elongate, tubular catheter body, an electrode for delivering or measuring an electrical signal, in particular an electrocardiac signal, via its external electrode contact surface, at least one first supply line for the electrical connection of the electrode, at least one second supply line for the electrical connection of a further electrode, a plug terminal connection between the at least one first supply line and the electrode, and an insulated passage of the at least one second supply line through the electrode.

16 Claims, 4 Drawing Sheets

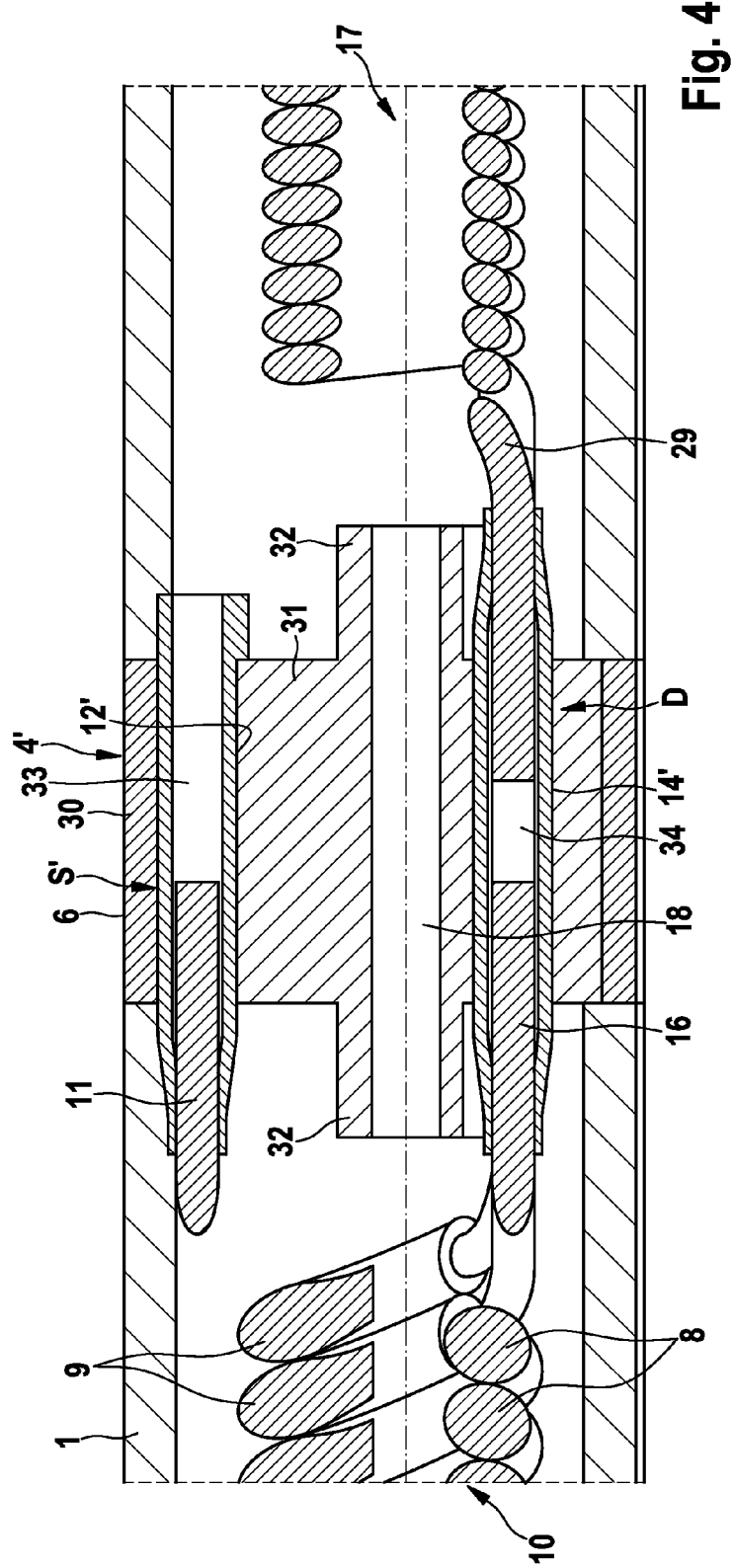

ELECTRODE CATHETER, IN PARTICULAR FOR CARDIAC THERAPY

RELATED APPLICATION

This patent application claims the benefit of co-pending U.S. Provisional Patent Application No. 61/378,406, filed on Aug. 31, 2010, which is hereby incorporated by reference in its entirety.

TECHNICAL FIELD

The invention relates to an electrode catheter, in particular for cardiac therapy, having the features specified in the preamble of the independent claim(s).

BACKGROUND

Such electrode catheters are known in greatly varying embodiments through public prior use, also of the present applicant, and comprise, as the basic components, an elongate, tubular catheter body, at least one electrode for delivering or measuring an electrical, in particular electrocardiac signal, via its external electrode contact surface, at least one first supply line for the electrical connection of this electrode, and at least one second supply line for the electrical connection of a further electrode. These electrodes are typically designed as two ring electrodes seated at the distal end of the electrode catheter with axial spacing, or one ring electrode and one head electrode, via which the stimulus conduction signals of the heart are measured or electrical pulses are delivered, for example, to end or otherwise treat an atrial flutter.

Three different types of supply lines are fundamentally known for the configuration of the electrode supply lines. The first type is the so-called coradial coil, in which the two supply lines are wound parallel to one another, similarly to a thread having two or more pitches, and are insulated from one another. In such coradial coils, the wires are deflected tangentially out of the coil composite and stripped to contact a ring electrode. The wires are then clamped between an inner sleeve and an outer sleeve and crimped or welded.

The connection and passage of the supply lines in such coradial coils has the disadvantage of the fact that tangentially leading the wires out and clamping them between two sleeves requires a comparatively large amount of installation space, which makes the goal of achieving the smallest possible, isodiametrical electrode diameter more difficult. Furthermore, the coil technology is very complex and thus cost-ineffective.

The second type of electrode supply line is the coaxial coil, which has a coiled inner conductor, which leads to a head electrode, for example, and a coiled outer conductor, which leads to a ring electrode situated proximally in front thereof. The coils are connected to the head or ring electrode using welding or crimping. This supply line type has the disadvantage of the fact that because of the two coils seated coaxially one inside the other, achieving the smallest possible electrode diameter in the millimeter range is problematic. This supply line technology can also be practically excluded for multipolar electrotypes.

Finally, a so-called multi-lumen construction is also known as a supply line technology, in which a tubular catheter body has at least two lumens along the electrode catheter. A thin wire cable runs through one of the two lumens to the ring electrode, and a coil is led through the other lumen to a head electrode, for example. The wire cable runs axially oriented to the coil and is welded or crimped to the ring electrode. The coil leads up to the electrode head and is also welded or crimped thereto.

This multi-lumen construction has the disadvantage of the fact that because of the maintenance of minimum wall thicknesses for the external insulation, the design of a multipolar electrode is difficult. Furthermore, the electrode construction is asymmetrical and no redundancy exists for the electrical contact of the ring electrode, because the ring electrode is only connected to the terminal plug via one cable. The durability of the contact between the supply line wire cable and the particular electrode can also be problematic.

U.S. Pat. No. 6,249,708 discloses a multiconductor electrode catheter, in which a central coil is led up to a head electrode and welded thereto. An insulating body is provided around this coil, which is provided with twisted grooves in its peripheral surface. Supply lines for a ring electrode are inserted in each of these. This design is also to be assigned to the coaxial coils having the above-described disadvantages.

U.S. Pat. No. 6,757,970 discloses a multiple electrode catheter, in which the electrode supply lines are led jointly in a multi-lead coil and the ends are led radially out of the coil composite. The contacting of the protruding ends is performed in a complex manner via bending over contact tabs on the strip-shaped ring electrodes, the protruding ends of the supply lines being clamped by the bending over. Subsequently, the strip configuration of the contacts must still be drawn by a tool for rolling into the elongate cylindrical form of the catheter. This design having its specific manner of manufacturing appears extremely difficult with respect to the filigree design of electrode catheters.

Proceeding from the described problems of the prior art, the invention is based on the object of attaching electrode supply lines to a ring electrode, for example, and simultaneously passing through supply lines for further electrodes situated distally to this electrode. Small isodiametrical electrode diameters are achievable through the design, as leading supply lines further to electrodes placed further distal is made more simple and, thus, overall a bipolar or multipolar electrode being able to be implemented using less effort in the contacting.

The present invention is directed at overcoming one or more of the above-identified problems.

SUMMARY

An object of the invention is achieved by the features of the independent claim(s) and the basic concept of a plug terminal connection between the first supply line and the corresponding electrode, and an insulated passage of the second supply line through this electrode.

Through this concept, the possibility advantageously results of implementing a change between various coils proximal and distal to an electrode, for example, from a fourfold coil proximal before an electrode to a twofold coil distal from this electrode. Bipolar and multipolar electrodes, as well as unipolar electrodes, may be implemented having identical electrode shapes, which results in a type of modular system. A compact construction having a correspondingly small external diameter of the electrode catheter can be achieved simultaneously.

Various other objects, aspects and advantages of the present invention can be obtained from a study of the specification, the drawings, and the appended claims.

DESCRIPTION OF THE DRAWINGS

The dependent claims characterize advantageous refinements of the invention, whose features, details, and advan FIGS. 2-4 show detailed, enlarged longitudinal axial sections of the electrode catheter in the area of a ring electrode in various embodiments.

DETAILED DESCRIPTION

Figure 1:
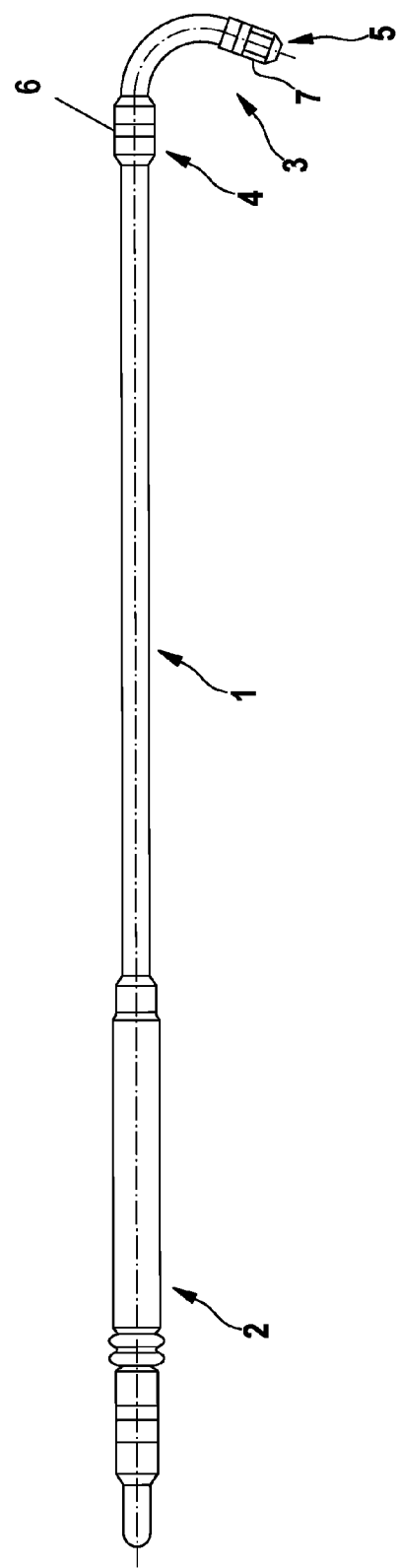
- FIG. 1 shows an overall view of a bipolar electrode catheter.

As shown in FIG. 1, in particular, the electrode catheter, which is used for cardiac therapy, has an elongate, tubular catheter body 1, which is provided on its proximal end with a terminal plug 2 for connection to a corresponding implant. A ring electrode 4 is situated in the area of the distal end 3 and a head electrode 5 is situated directly on the tip of the distal end 3. These electrodes 4 and 5 are used for delivering or measuring an electrical signal, thus, in the present case, an electrocardiac signal, via their external electrode contact surface 6 and 7, respectively, for reliable and effective defibrillation, for example, or a diagnosis for early recognition of atrial flutter and a cardiac insufficiency progression.

Figure 2:
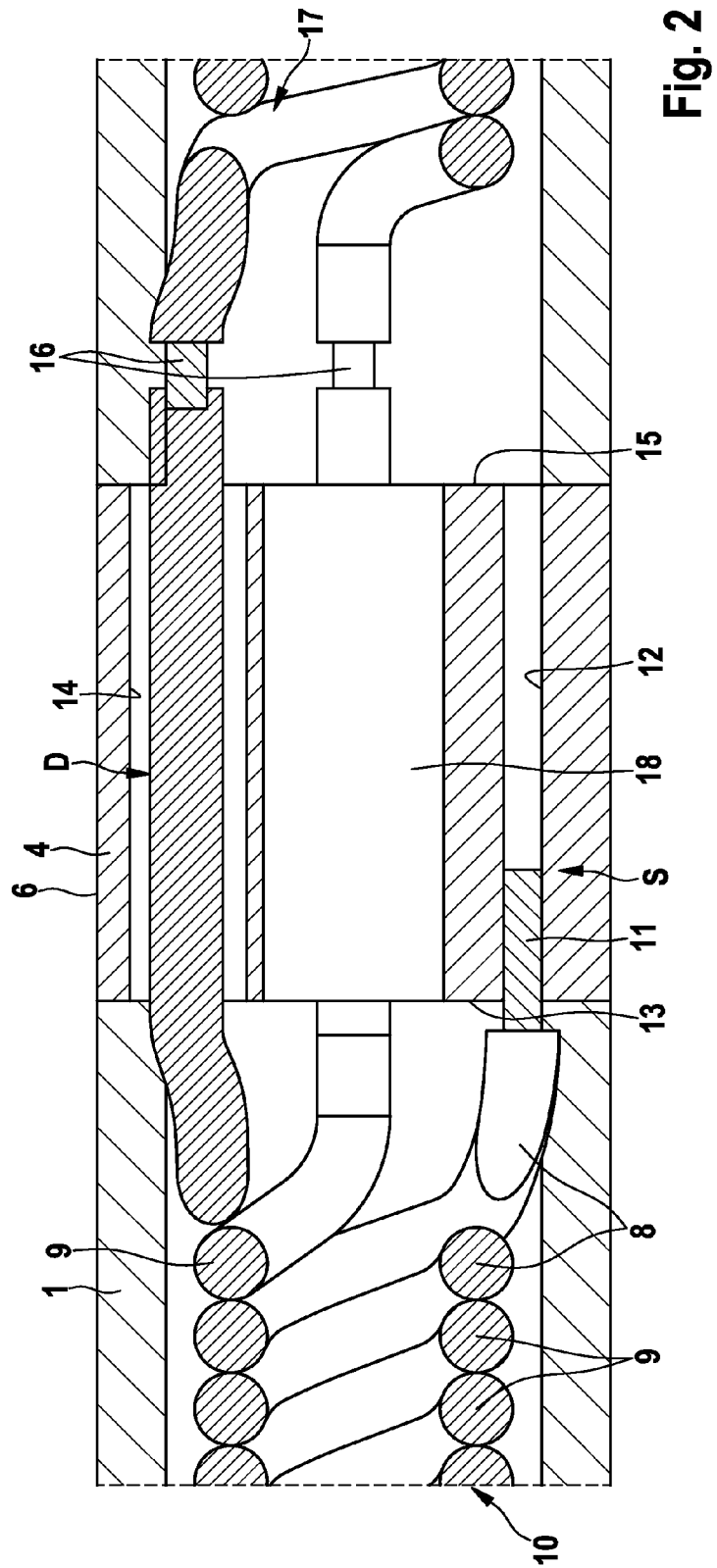

A first embodiment for the attachment of the electrodes 4, 5 to corresponding supply lines 8 and 9 is to be explained on the basis of FIG. 2. Thus, two supply lines 8 and 9, in the form of a fourfold coil 10, are led into the tubular catheter body 1 from a proximal location. The two supply lines denoted by reference numeral 8 for the ring electrode 4 are coupled with the aid of a plug terminal connection S, to be explained in greater detail hereafter, to the ring electrode 4. The two supply lines denoted by reference numeral 9 for the head electrode 5 (see FIG. 1), which is not shown in FIG. 2, are led through the ring electrode 4 from proximal to distal with the aid of a passage designated as a hole by D.

The two supply lines 8 are led away in the axial direction from the fourfold coil 10 and their ends 11 are stripped. The particular stripped end is inserted into an axially-parallel receptacle hole 12 or receptacle having an annular front face 13 of the ring electrode 4, which is inside the catheter body 1, and connected thereto by a material bond, for example, by lasers or resistance welding, to form a secure contact and in a mechanically fixed manner.

For the two supply lines 9 of the head electrode 5, longitudinally-axially-parallel passage holes 14 are provided in the ring electrode 4, which run between the proximal front face 13 and the distal front face 15 of the ring electrode 4. The supply lines 9, which are led away axially-parallel from the fourfold coil 10, are lead using the insulated, linear leg through the passage hole 14. Their stripped ends 16 are connected to a twofold coil 17, which leads further isodiametrically up to the head electrode 5 (not shown) and is attached accordingly thereto. The electrical contact between the end 16 of the supply lines 9 and the twofold coil 17 can be produced via a material bond, for example.

The central opening 18 of the ring electrode 4 is used—precisely like the inner openings of the coils 10 and 17—for the passage of the mandrin or guide wires for the electrode catheter.

This type of contacting may also be transferred to the electrode head and to the plug to a cardiac pacemaker device. The electrode catheter can thus be constructed in its design as a modular system.

Figure 3:
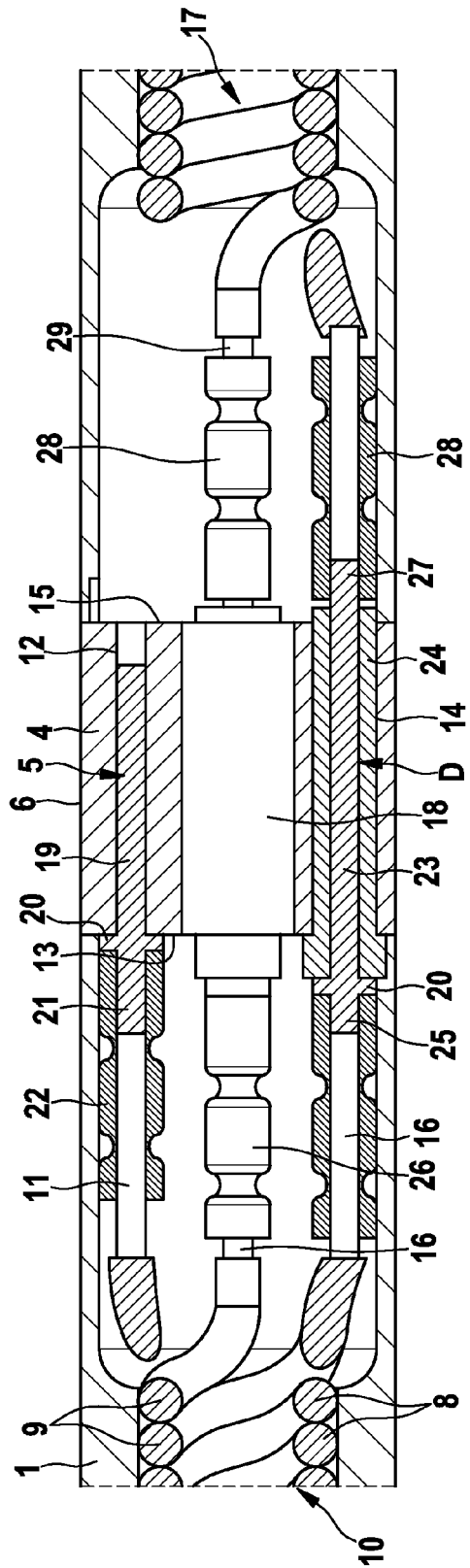

The embodiment of the plug terminal connection S and the passage D for the supply lines 8 and 9 shown in FIG. 3 is fundamentally based on a crimping technique. Thus, the ring electrode 4 again has two parallel receptacle or passage holes 12 and 14 running longitudinally-axial between the proximal and distal front faces 13 and 15. A metal crimping shaft 19, which is connected to form an electrical contact with the ring electrode 4 and is mechanically fixed by a press fit or a material bond in the receptacle holes 12, is seated in each of the receptacle holes 12. The insertion depth of the crimping shaft 19 is limited by a stop shoulder 20. Outside the receptacle holes 12, the crimping shaft 19 has a crimping pin 21. The stripped ends 11 of the supply line 8 for the ring electrode 4 are inserted into a crimping sleeve 22, which is seated on the crimping pin 21. Through typical crimping of the crimping sleeve 22, a secure mechanical and electrical connection is provided between the ends 11 of the supply lines 8 and the crimping shaft 19. This crimped attachment of the wires to the electrode can also be designed as a welded attachment employing similar components.

For the passage of the supply lines 9 for the head electrode 5 (see FIG. 1), which is not shown in FIG. 3, a corresponding crimping shaft 23 having an insulating sleeve 24 surrounding it is inserted into the passage holes 14 in the ring electrode 4. The assembly made of the crimping shaft 23 and insulating sleeve 24 is held stably in the passage holes 14 by pressing it in, for example. The insertion depth of the crimping shaft 23 into the insulating sleeve 24 is again limited via a stop shoulder 20, outside of which a crimping pin 25 is implemented proximally. Similarly to the attachment of the supply lines 8, the stripped ends 16 of the supply lines 9 are also inserted into a crimping sleeve 26, which is seated on the crimping pin 25. By crimping this crimping sleeve 26, a mechanically and electrically stable connection is provided between the supply lines 9 and the corresponding crimping shafts 23.

The distal end 27 of the crimping shaft 23 protrudes beyond the insulating sleeve 24 and is used, together with a crimping sleeve 28 plugged thereon, for attaching the stripped wires which are led away axially from the twofold coil 17 leading distally to the head electrode 5.

The ring electrode 4 according to FIG. 3 also has a central opening 18 for the passage of the mandrin and guide wires.

While the ring electrode 4 according to FIGS. 2 and 3 is implemented as a solid electrode, in the embodiment shown in FIG. 4, the ring electrode 4' is provided with an external, thin-walled electrode ring 30, which forms the electrode contact surface 6. An essentially cylindrical core 31 made of insulating plastic, whose axial length in the peripheral area corresponds to that of the electrode ring 30, is seated in the ring opening. An opening 18 is provided centrally on the core 31, which is lengthened by corresponding collar projections 32 in relation to the axial length of the core 31. This opening 18 is again used for the passage of the mandrin and guide wires.

For the attachment of the two supply lines 8 of the ring electrode 4', axially-parallel receptacle holes 12', which are open radially outward in a slotted manner, are provided in the area of the periphery of the core 31, into which metal crimping sleeves 33 are inserted. These crimping sleeves 33 thus press against the electrode ring 30 and thus produce an electrical connection thereto. The stripped ends 11 of the supply lines 8 are plugged into these crimping sleeves 33 and are mechanically and electrically fixedly connected thereto by corresponding crimping.

For the passage D of the supply lines 9 to the head electrode 5, passage holes 14' are introduced in an axially-parallel manner in the core 31, and are positioned with radial spacing from the central axis and the electrode ring 30. The crimping sleeve 34 is seated thereon and is thus situated electrically insulated from the electrode ring 30. The stripped ends 16 of the supply lines 9 are plugged in the proximal ends of the crimping sleeves 34. The stripped ends 29 of the twofold coil 17 are plugged into thee distal ends of the crimping sleeves 34. A mechanically and electrically secure connection between the twofold coil 17 and the supply lines 9 is provided by corresponding crimping of the crimping sleeves 34 on their distal and proximal ends. This crimped attachment of the wires to the electrode can also be designed as a welded attachment employing similar components.

For the sake of good order, it is to be noted that in FIG. 4, of the two plug terminal connections S and two passages D, only a single one is recognizable in the sectional view. Furthermore, it is to be noted that the plug terminal connections S and the passages D according to FIGS. 2 and 3 are mutually exchangeable, i.e., a plug terminal connection S according to FIG. 2 can be combined with the passage D according to FIG. 3, and vice versa.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An electrode catheter for cardiac therapy, comprising:
    an elongate, tubular catheter body having a central bore there through;
    an electrode for delivering or measuring an electrocardiac signal via its external electrode contact surface, the electrode having a central bore there through in alignment with the central bore of the catheter body;
    at least one first supply line for the electrical connection of the electrode;
    at least one second supply line for the electrical connection of a further electrode;
    a plug terminal connection between the at least one first supply line and the electrode; and
    an insulated passage of the at least one second supply line through the electrode, wherein the insulated passage is separate, and axially offset, from the central bore of the electrode.

2. The electrode catheter according to claim 1, wherein the plug terminal connection is designed as a receptacle hole or receptacle groove in a front face of the electrode, located in the catheter body, into which a stripped end of the at least one first supply line is inserted and fixed.

3. The electrode catheter according to claim 1, wherein the plug terminal connection is designed as a crimped connection, which has a crimping shaft, seated in the electrode, having a crimping pin protruding from a front face of the electrode, located in the catheter body, and a crimping sleeve, which connects the crimping pin and a stripped end of the at least one first supply line.

4. The electrode catheter according to claim 3, wherein the crimping shaft has a stop shoulder for limiting its insertion depth into the electrode.

5. The electrode catheter according to claim 1, wherein the electrode is implemented as a solid ring electrode.

6. The electrode catheter according to claim 1, wherein the electrode has an external, thin-walled electrode ring and an insulating core, a crimping sleeve or welding sleeve having electrical contact to the electrode ring being situated in a receptacle hole of the core, which is open toward the electrode ring, and being crimped or welded to a stripped end of the at least one first supply line.

7. The electrode catheter according to claim 6, wherein the at least one second supply line is led through the insulating core with radial spacing to the electrode ring.

8. The electrode catheter according to claim 7, wherein a crimping sleeve in the insulating core is led through with radial spacing to the electrode ring, which is crimped proximally with a stripped end of the at least one second supply line and distally with a stripped end of a distal line leading further along a length of the electrode catheter.

9. The electrode catheter according to claim 1, wherein the insulated passage for the at least one second supply line is implemented as a through hole through the electrode, through which the at least one insulated second supply line is led.

10. The electrode catheter according to claim 9, wherein the at least one second supply line, which is led through the through hole, is connected distally from the insulated passage to a conductor coil, which leads further along a length of the electrode catheter.

11. The electrode catheter according to claim 1, wherein the insulated passage for the at least one second supply line is formed by an insulated crimping shaft led through the electrode, which has:
    proximally, a crimping pin protruding from a front face of the electrode in the catheter body, and a crimping sleeve, which connects the proximal crimping pin and a stripped end of the at least one second supply line; and
    distally, a crimping pin protruding from a further front face of the electrode in the catheter body, and a crimping sleeve connecting the distal crimping pin and a stripped end of a distal line leading further along a length of the electrode catheter.

12. The electrode catheter according to claim 11, wherein the crimping shaft has a stop shoulder for limiting its insertion depth into the electrode.

13. The electrode catheter according to claim 1, wherein the at least one first and second supply lines each comprise a plurality of coils.

14. The electrode catheter according to claim 1, wherein the at least one first and second supply lines are led jointly as a coradial multiple coil from proximally to the electrode.

15. The electrode catheter according to claim 14, wherein the ends of the at least one first and second supply lines to be connected to the electrode or led through it are led out of the coil composite longitudinally-axially-parallel.

16. The electrode catheter according to claim 1, wherein the at least one second supply line, which is led through the electrode, is connected to a distal coil line leading further along a length of the electrode catheter.

\* \* \* \* \*